(12) United States Patent
Weber et al.

(10) Patent No.: US 10,905,846 B2
(45) Date of Patent: Feb. 2, 2021

(54) PHOTOTHERAPY SLEEP MASK

(71) Applicants: Cornelia Weber, Franklin, TN (US); Dale Weber, Franklin, TN (US)

(72) Inventors: Cornelia Weber, Franklin, TN (US); Dale Weber, Franklin, TN (US)

(*) Notice: Subject to any disclaimer, the term of this patent is extended or adjusted under 35 U.S.C. 154(b) by 0 days.

(21) Appl. No.: 15/428,057

(22) Filed: Feb. 8, 2017

(65) Prior Publication Data
US 2017/0224951 A1    Aug. 10, 2017

Related U.S. Application Data

(60) Provisional application No. 62/292,759, filed on Feb. 8, 2016.

(51) Int. Cl.
*A61M 21/02*    (2006.01)
*A61N 5/06*     (2006.01)
*A61M 21/00*    (2006.01)
*A61N 5/067*    (2006.01)

(52) U.S. Cl.
CPC ........... *A61M 21/02* (2013.01); *A61N 5/0618* (2013.01); *A61M 2021/0044* (2013.01); *A61M 2210/0612* (2013.01); *A61N 2005/067* (2013.01); *A61N 2005/0626* (2013.01); *A61N 2005/0648* (2013.01); *A61N 2005/0651* (2013.01); *A61N 2005/0662* (2013.01)

(58) Field of Classification Search
CPC .... A61N 2005/0648; A61N 2005/0662; A61N 2005/0651; A61N 2005/067; A61N 5/0618; A61N 2005/0626; A61M 2230/18; A61M 21/02; A61M 2210/0612; A61M 2021/0044; A61B 5/0478; A61B 5/6821

USPC ................................................ 600/26–28
See application file for complete search history.

(56) References Cited

U.S. PATENT DOCUMENTS 4,858,609 A * 8/1989 Cole ................. A61M 21/00
                                                 607/91
5,259,830 A * 11/1993 Masuda ............ A61M 21/00
                                                 600/27
(Continued)

OTHER PUBLICATIONS

International Search Report and Written Opinion, PCT/US2017/017056, Weber (international filing date Feb. 8, 2017).
(Continued)

*Primary Examiner* — Navin Natnithithadha
*Assistant Examiner* — Sunita Reddy
(74) *Attorney, Agent, or Firm* — Wayne Edward Ramage; Baker Donelson

(57) ABSTRACT

A phototherapy mask adapted to fit over the eye area of the user. The mask comprises a plurality of semiconductor light sources such as, but not limited to, light-emitting diodes (LEDs) or laser diodes, fiber optics, full spectrum light sources, RGB LEDs, piezo transducers, vibrational transducers (ultrasonic or otherwise), or a combination thereof, that provide therapeutic and rejuvenating effects to human tissue. The light sources are arranged so as to focus on the eye areas, and light enters through the eyes (open or closed). The light sources emit energy in the form of photons when switched on, which deliver energy to targeted tissue, penetrating the layers of skin and the eyes to produce a non-thermal photochemical effect at the cellular level.

10 Claims, 5 Drawing Sheets

(56) References Cited

U.S. PATENT DOCUMENTS

| | | | | |
|---|---|---|---|---|
| 5,507,716 A * | 4/1996 | LaBerge | A61M 21/00 | 600/27 |
| 5,518,497 A * | 5/1996 | Widjaja | A61M 21/00 | 600/26 |
| 6,350,275 B1 * | 2/2002 | Vreman | A61M 21/00 | 607/88 |
| 2004/0225340 A1 * | 11/2004 | Evans | A61M 21/00 | 607/88 |
| 2005/0278003 A1 * | 12/2005 | Feldman | A61M 21/02 | 607/88 |
| 2006/0259100 A1 | 11/2006 | Hilburg | | |
| 2007/0270683 A1 * | 11/2007 | Meloy | A61B 5/0555 | 600/415 |
| 2009/0223518 A1 | 9/2009 | Kwok et al. | | |
| 2010/0076253 A1 * | 3/2010 | Altman | A61M 21/00 | 600/28 |
| 2011/0040356 A1 * | 2/2011 | Schiffer | A61N 5/0618 | 607/88 |
| 2011/0257712 A1 | 10/2011 | Wells et al. | | |
| 2011/0257713 A1 * | 10/2011 | Clegg | A61M 21/02 | 607/90 |
| 2012/0222192 A1 * | 9/2012 | Carey | A61F 7/02 | 2/171.2 |
| 2012/0327367 A1 * | 12/2012 | Anschel | A61N 5/0622 | 351/221 |
| 2013/0053929 A1 * | 2/2013 | Colbaugh | A61M 21/02 | 607/90 |
| 2013/0066404 A1 * | 3/2013 | Tapper | A61N 5/0616 | 607/90 |
| 2013/0184516 A1 * | 7/2013 | Genereux | A61M 21/02 | 600/28 |
| 2013/0303837 A1 * | 11/2013 | Berka | A61M 21/02 | 600/28 |
| 2014/0316192 A1 * | 10/2014 | de Zambotti | G06F 19/00 | 600/28 |
| 2014/0350643 A1 * | 11/2014 | Pepitone | A61N 5/0616 | 607/89 |
| 2015/0209597 A1 | 7/2015 | Haarlander et al. | | |
| 2015/0335910 A1 * | 11/2015 | Tapper | A61N 5/0616 | 607/90 |
| 2016/0045759 A1 * | 2/2016 | Tapper | A61N 5/0616 | 607/90 |
| 2016/0193442 A1 * | 7/2016 | Adamczyk | A61M 21/02 | 600/27 |
| 2016/0270656 A1 * | 9/2016 | Samec | A61B 3/085 | |
| 2017/0209333 A1 * | 7/2017 | Shoup | A61N 2/002 | |

OTHER PUBLICATIONS

Rojas, et al., "Low Level Light Therapy of the Eye and Brain," Eye and Brain 2011:3 49-67 (Oct. 14, 2011).

Hashmi, et al., "Role of Low-Level Laser Therapy in Neurorehabilitation," PM R Dec. 2, 2010 (12 Supp. 2) S292-S305 (Dec. 2, 2010).

American Society for Laser Medicine and Surgery, "Photobiomodulation—Low Level Light Therapy (LLLt)," http://www.aslms.org/public/LowLevelLight.shtml (Jun. 3, 2010).

* cited by examiner

PHOTOTHERAPY SLEEP MASK

This application claims benefit of and priority to U.S. Provisional Application No. 62/292,759, filed Feb. 8, 2016, by Cornelia Weber, et al., and is entitled to that filing date for priority. The specification, figures, appendices and complete disclosure of U.S. Provisional Application No. 62/292,759 are incorporated herein in their entireties by specific reference for all purposes.

FIELD OF INVENTION

This invention relates to a sleep mask and related methods for phototherapy or light therapy applications to the face and eye area to promote sleep and other health effects.

BACKGROUND OF THE INVENTION

Physicists have recognized light to be a pure form of energy that is a part of the electromagnetic radiation spectrum. Within this spectrum, the various colors of light each represent unique wavelengths and frequencies that produce therapeutic effects when absorbed through the skin of the body. Near infrared wavelengths are longer than visible light wavelengths, and have been found to penetrate to a deeper level of muscle, bones and joints. Visible red light tends to stimulate growth at the cellular level whereas blue light has more of a soothing affect.

Further scientific research has found that the application of low-level light therapy on the body produces a photochemical reaction in the cell. During this process, photons of light are absorbed into the treated cell to increase and stimulate stored energy. As a result, this stored energy transforms into chemical energy that can be used to regulate cellular activity; including enhanced ATP synthesis, protein synthesis, cellular proliferation, and growth factor secretion.

Low-level light therapy increases energy; reduces pain and inflammation; and reduces stress, as documented in the following reports, the abstracts of which are attached as appendices to U.S. Provisional Application No. 62/292,759, and which are incorporated herein by specific reference for all purposes:

Rojas, et al., "Low Level Light Therapy of the Eye and Brain," Eye and Brain, Oct. 14, 2011 (19 pages).

Hashmi, et al., "Role of Low-Level Laser Therapy in Neurorehabilitation," PM R 2010 Dec. 2 (12 Supp. 2) S292-S305 (17 pages).

ASLMS, "Photobiomodulation—Low Level Light Therapy (LLLT)," http://www.aslms.org/public/LowLevel-Light.shtml (Jun. 3, 2010) (2 pages).

SUMMARY OF INVENTION

In various exemplary embodiments, the present invention comprises a mask adapted to fit over the eye area of the user. The mask comprises a plurality of semiconductor light sources, such as, but not limited to, light-emitting diodes (LEDs) or laser diodes, fiber optics, full spectrum light sources, RGB LEDs, piezo transducers, vibrational transducers (ultrasonic or otherwise), or a combination thereof, that provide therapeutic and rejuvenating effects to human tissue. The light sources are arranged so as to focus on the eye areas, and light enters through the eyes (open or closed). The light sources emit energy in the form of photons when switched on, which deliver energy to targeted tissue, penetrating the layers of skin and the eyes to produce a non-thermal photochemical effect at the cellular level. In one exemplary embodiment, red light is used to promote sleep due to the effect of red light on not interrupting the production of melatonin (i.e., the mask is used as a sleep mask). The therapy is noninvasive, and avoids the potential side effects of older forms of therapy, such as drug therapy. The mask may be held in place in a variety of ways known in the art, such as straps, bands, arms, or clips. In one embodiment, the mask may be weighted. Power for the invention may be provided by plugging the device into a standard electrical outlet. Alternatively, one or more batteries may be provided.

DETAILED DESCRIPTION OF EXEMPLARY EMBODIMENTS

Figure 1:
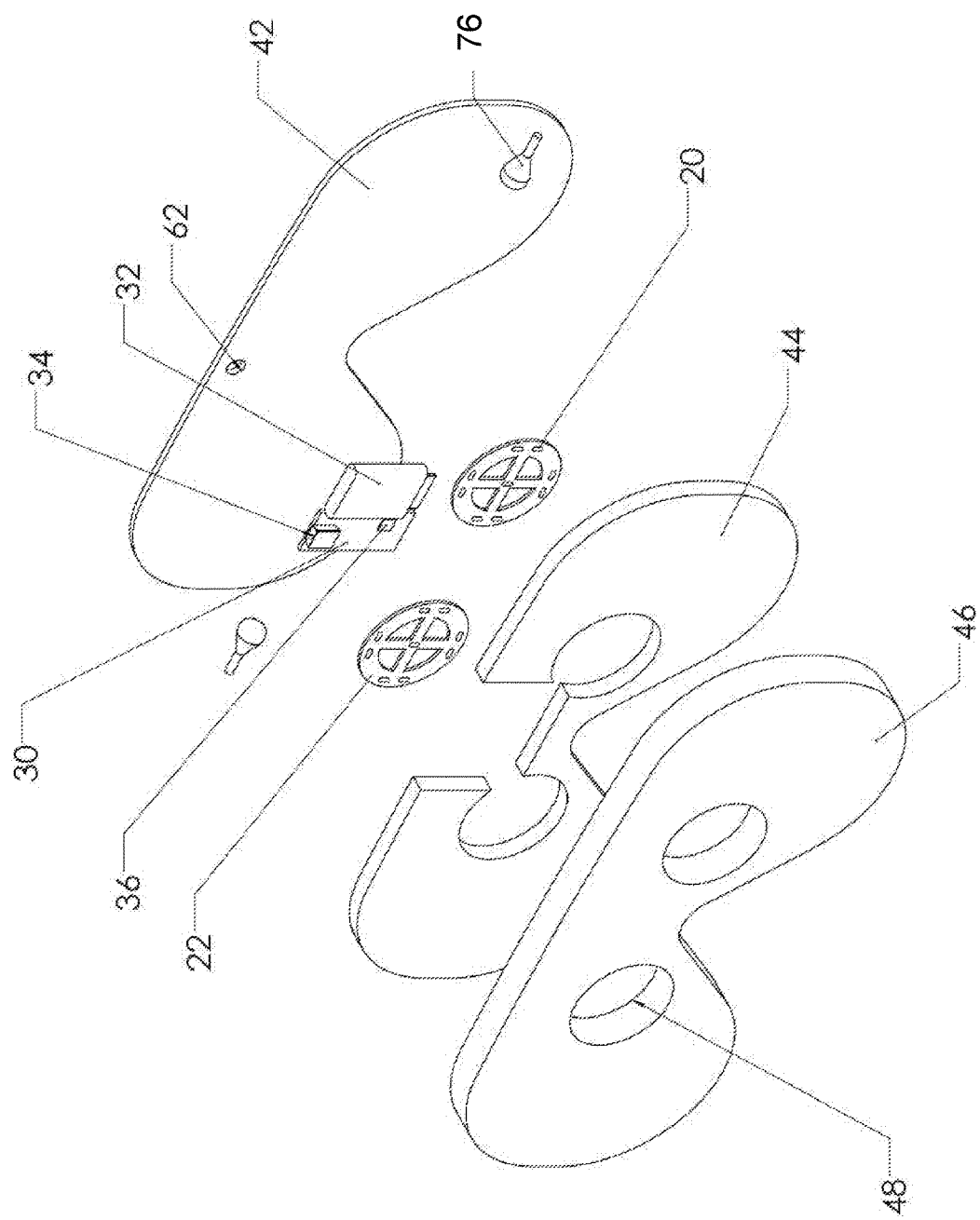
FIG. 1 shows a exploded view of a mask in accordance with an embodiment of the present invention.
Figure 2:
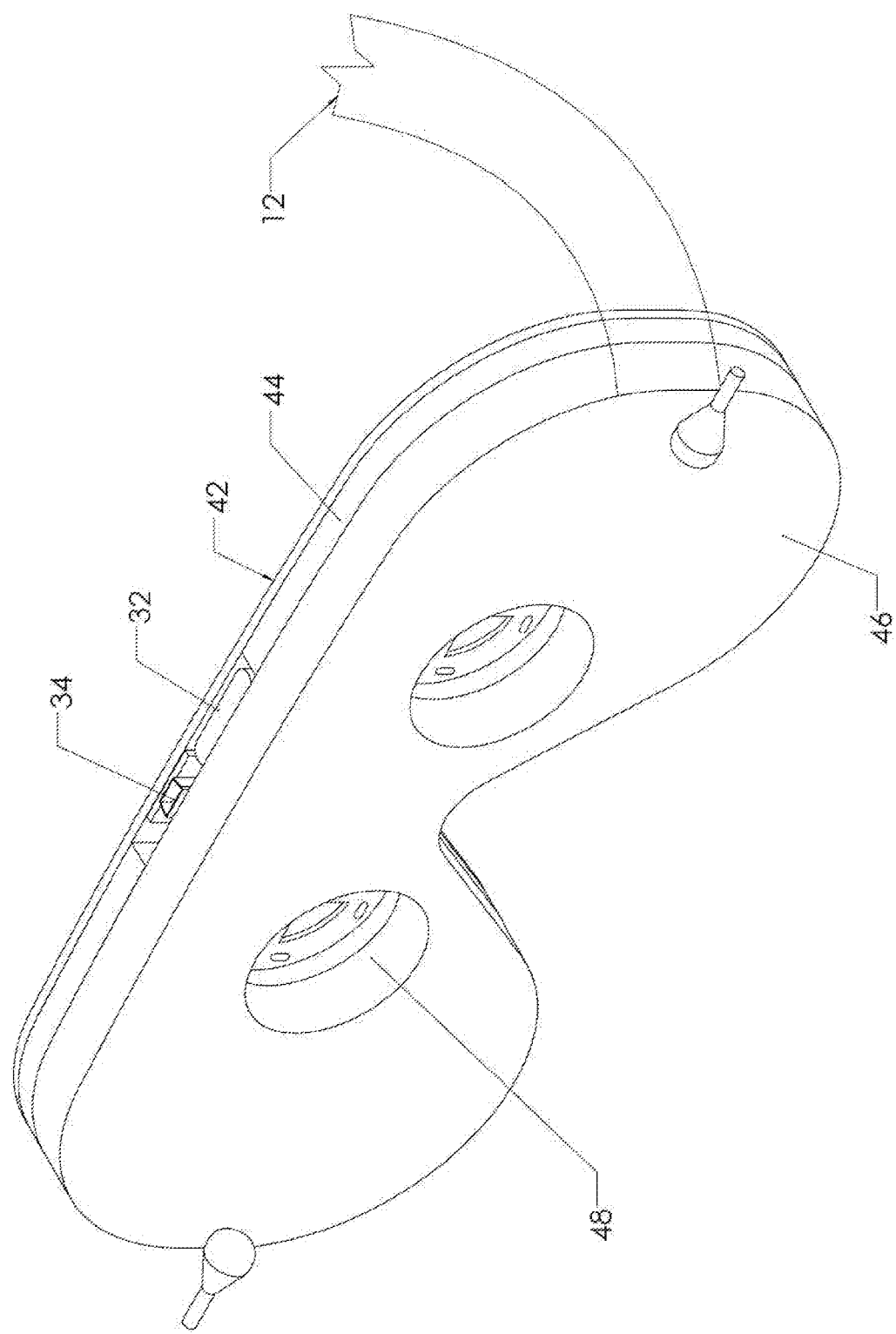
FIG. 2 shows a perspective view of the mask of FIG. 1.
Figure 3:
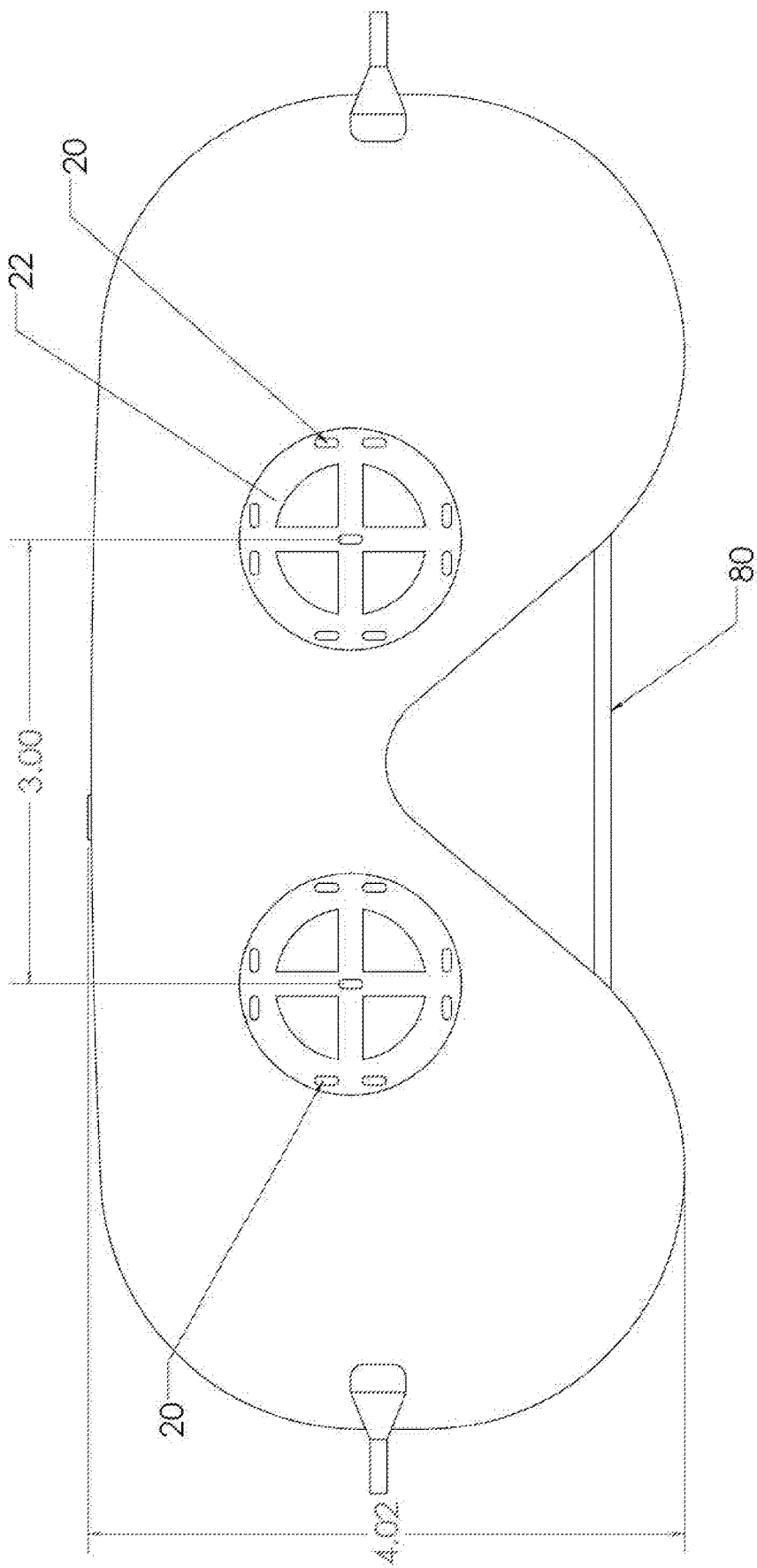
FIG. 3 shows an inner view of the mask of FIG. 1 with an aromatherapy component.
Figure 4:
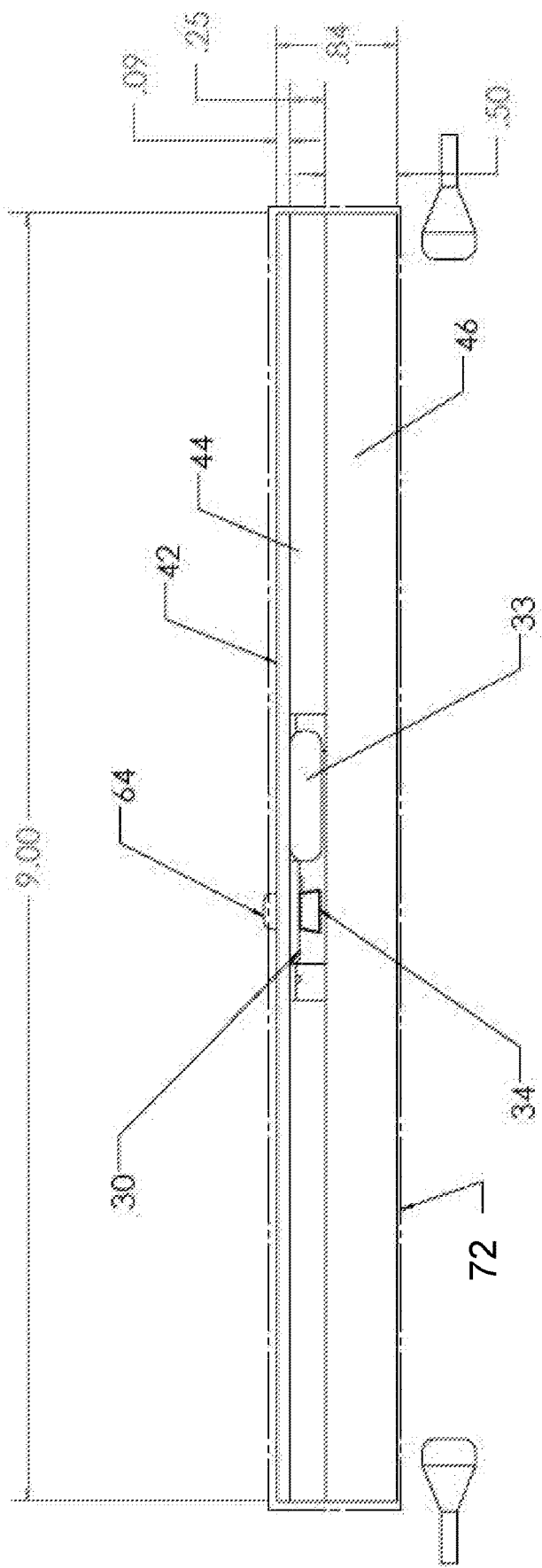
FIG. 4 shows a side edge view of the mask of FIG. 1.

In various exemplary embodiments, the present invention comprises a mask adapted to fit over the eye area of the user. The mask comprises a plurality of semiconductor light sources 20, such as, but not limited to, light-emitting diodes (LEDs) or laser diodes, fiber optics, full spectrum light sources, RGB LEDs, piezo transducers, vibrational transducers (ultrasonic or otherwise), or a combination thereof, that provide therapeutic and rejuvenating effects to human tissue. The light sources 20 are arranged so as to focus on the eye areas, and light enters through the eyes (open or closed). The light sources emit energy in the form of photons when switched on, which deliver energy to targeted tissue, penetrating the layers of skin and the eyes to produce a non-thermal photochemical effect at the cellular level. In one exemplary embodiment, red light is used to promote sleep due to the effect of red light on not interrupting the production of melatonin (i.e., the mask is used as a sleep mask). The therapy is noninvasive, and avoids the potential side effects of older forms of therapy, such as drug therapy.

The mask may be held in place in a variety of ways known in the art, such as straps 12, bands, arms, or clips. In one embodiment, the mask may be weighted. Power for the invention may be provided by plugging the device into a standard electrical outlet. Alternatively, one or more batteries 32 may be provided.

As seen in FIGS. 1-4, in one exemplary embodiment the mask comprises an outer layer 42, an inner layer 46 with one or two holes 48 to allow light from the light sources to reach the eyes, and a middle layer 44 sandwiched between the outer and inner layers. One or two light source boards 22 may be affixed to or disposed on the middle or other layer, each board with an array of light sources 20 thereon. The middle layer also may comprise a circuit or control board 30, with one or more rechargeable energy sources 32 (e.g., battery), recharging ports or plugs, communications ports (e.g., USB or mini-USB 34) and/or wireless communications chips 36.

In several exemplary embodiments, the outer layer 42 may be opaque in whole or in part to prevent outside illumination from reaching the user's eyes. One or more holes 62 may be provided in the outer layer to allow access to communications ports or recharging ports, on/off or reset switches 64, or device controls, as described above. Alternatively, the ports, plugs, switches and controls may be accessible along the side or top of the middle layer. The outer layer and middle layer may be made of any suitable material, including but not limited to plastic, neoprene, foam, memory foam, cardboard, rubber, fabric, or combinations thereof. The inner layer may be made of similar materials.

The layers may be bonded or attached by various means known in the art. In one embodiment, one or all layers may be detachable from each other. The layers may be enclosed in a sleeve or bag 72 for comfort in use.

In the embodiment shown, a plurality of light sources 20 are arrayed on an interior-facing circular circuit boards 22, which can be secured to one or more of the layers by various means known in the art, including, but not limited to, thread, rivet, adhesive, glue, encasement in a plastic injected molded frame, VHB tape, or other means. The light sources may be covered with a clear cover, made of glass, plastic or similar material. The circuit boards may be detachable from the middle layer or other layers, and circuit boards may be interchangeable. Various circuit boards contain various configurations or patterns of light sources, in a variety of colors and intensities (i.e., milliwatts range). Examples of light source orientation thus include, but are not limited to, a fixed straight position, or a variety of angled positions (i.e., with respect to the circuit board eye plate) allowing bi-directional ability of light to crisscross.

The circuit boards also may vary in size and shape. Different colors may be used for different treatments. The circuit boards are interchangeable by the user as desired. Alternatively, the light sources may be RGB LEDs, which can produce different colors and intensities as desired or programmed The device can be presented in a variety of forms, including a simple mask or goggle configuration with arms to fit behind the ears, or a strap that fits around the head. In an alternative configuration, the device may be secured by a strap or band that fits over the top of the head. The device may come in various sizes and configurations to suit different users. In one exemplary embodiment, the device is approximately 9 inches long, approximately 4 inches in height, approximately 0.80 to 0.90 inches thick (0.84 inches in one embodiment), with light source circuit boards spaced 3 inches apart (from center to center). In one embodiment, the inner layer is approximately 0.5 inches thick, the middle layer is approximately 0.25 inches thick, and the outer layers is 0.09 inches thick.

In several embodiments, one or two earbuds or earphones" 76 also may be attached in the appropriate positions. The earbuds or earphones comprise speakers to provide music, radio, or other sound while the user is wearing the device. The earbuds or earphones may be connected by wire to the mask or strap, band, or arms, or to a sound reproduction device, or may be independent or standalone and connected wirelessly to a sound reproduction device. The sound reproduction device may be separate from the mask (e.g., iPod, iPhone, mobile device, mpg player, or the like), or may be included in the mask or sleeve.

The earbuds or earphones may also contain various light sources, as described above. The device also may contain optical fibers to carry light to the ear buds or earphones. Light sources may be placed in a variety of configurations or patterns, in a similar manner as described above, to allow light to enter through the ears and thereby impact the inner ear and brain, or to illuminate the area around and outside of the ear. Removable faceplates, as described above, may also be used with the earbuds or earphones.

In one embodiment, an area, strap, piece or component 80 just below the nose line extends from one side of the lower bottom (or near the lower bottom) of the facemask unit to the other. This area allows the placement of essential oils or the like to delivery aroma therapy to nose and areas around the eyes for additional sensations to the body, nose, and surrounding tissue.

Figure 5:
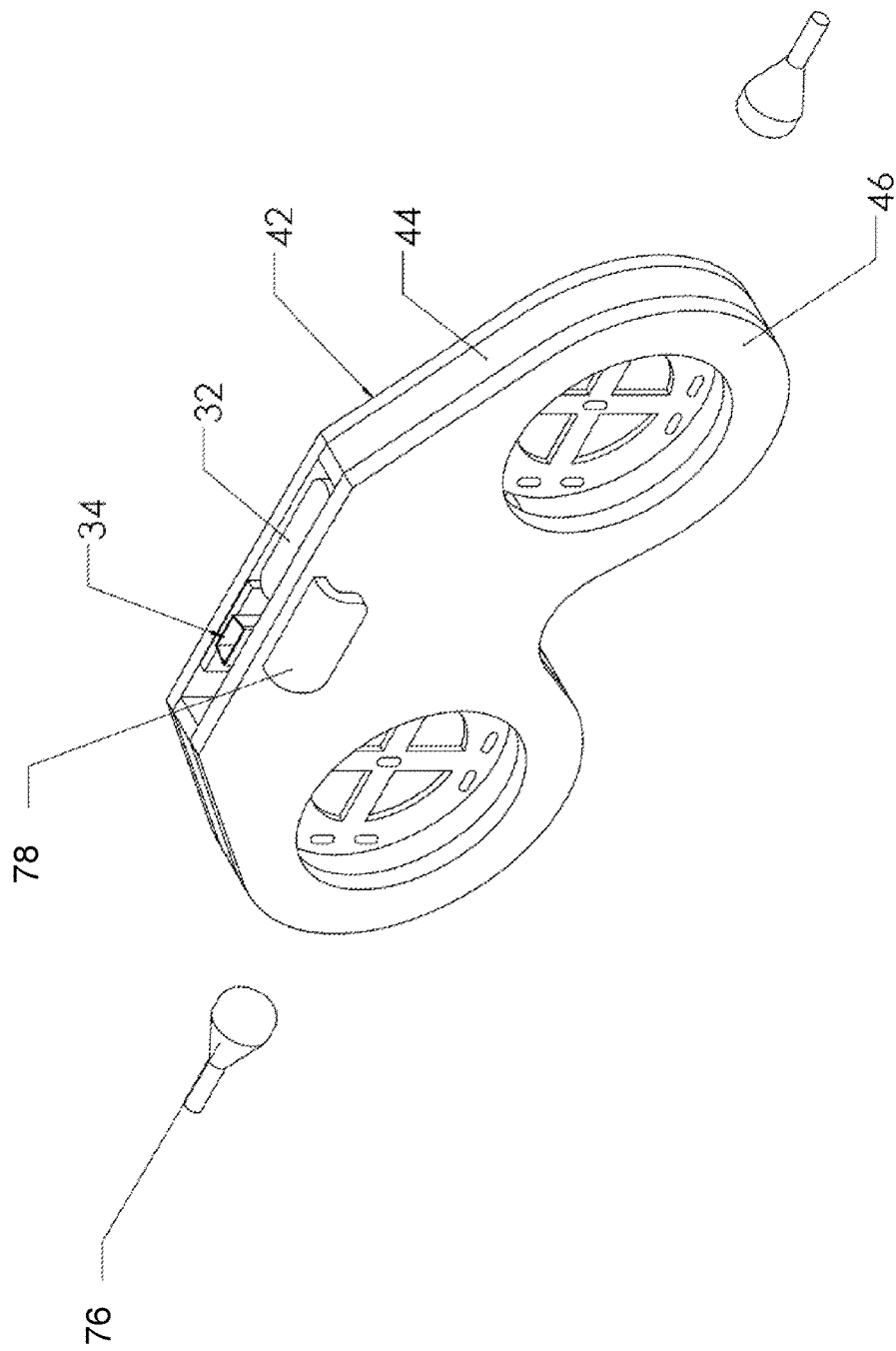
FIG. 5 shows a perspective view of an embodiment of a mask with an eyeglass attachment clip.

In a further embodiment, as seen in FIG. 5, the invention comprises one or more layers (as described above) forming a fully contained unit that slides over or is mounted on existing eyeglass frames (not shown) for maximum portability. In the embodiment shown, for example, the fully contained unit is attached to the top of existing eyeglass frames by means of a clip 78 extending from the inner or outer layer. The fully contained unit can be placed inside or outside of the glass lenses on the eyeglass frame.

The device may comprise a number of individual light sources. The configuration or patterns of light sources can vary, as well as the color and intensities (i.e., milliwatt ranges) of the light sources. Likewise, the light sources can comprise various mixes of types of light sources (e.g., all LEDs, all laser diodes, all fiber optics, or a combination thereof). Different colors and intensities may be used for different treatments. In addition, different colors and intensities may be used in different areas.

The light sources can be controlled by wireless or wired connection with a computing device operating a control program, a touchpad monitor or device on or connected to the device, or a control unit on the device itself. The user can control color, type, duration, wavelength amplitude, wavelength phase, and frequency (pulse) of the light sources being activated during therapeutic application, as described in further detail below.

For portable operation, light and frequency settings as well as visualization recordings may be embedded into the unit itself through a scan disk or can be uploaded from a software device to contain specific frequencies and light patterns. The phototherapy mask device has the capacity to accept a scan disk drive or similar technology to store information such as music, MP3 files, and any other type of material for use with the device. The information can come from any source but not limited to a microcontroller in the device embedded into the eye mask unit or coming from another external devices either through the use of WiFi, or Bluetooth, or Li-Fi (Light Fidelity). Li-Fi is a bidirectional, high speed and fully networked wireless communication technology similar to Wi-Fi.

In one embodiment, the present invention utilizes RGB technology. RGB technology utilizes the color mixing properties of red, green, and blue LED chips that are provided on a reflector. A photomixing material and filler resin scatters the light rays to uniformly combine the rays emitted from the LED chips. The photomixing material and filler resin are applied onto upper sides of the light emitting diode chips while being mixed with each other, and the photomixing material is uniformly dispersed in the filler resin.

In several embodiments, the light sources include red, blue, green and orange colors. These colors have the following effects:

Red: stimulates vitality and growth; good for fatigue and debilitating conditions; use for deficient nutrition, dormant conditions, poor appetite, constipation, depression, drowsiness, and paralysis.

Blue: slows down growth; calming; acts as a sedative; relieves excitement and inflammation; resets "biological clock" of the human body using doses of 20 minutes; blue light to Alzheimer's patients helped biological clock to sleep longer at night; use for nervousness, irritability, fussiness, feverishness; apply to all conditions where inflammation is present; use for internal bleeding, nervous conditions.

Green: slows down growth; calming; relieves excitement and inflammation; useful when combined with blue/red and yellow as a brain/nerve stimulate and laxative.

Orange: a combination of red and yellow is powerful in colds and sluggish/chronic conditions as it helps release stored energy.

In one embodiment, the invention can run any light frequency within the pulsing range of 0 Hz to 100,000,000,000 Hz, and can run all safe wavelengths of the electromagnetic spectrum, including visible light and near-infrared light. In one exemplary embodiment, the power output per laser diode, LED, or fiber optic ranges from 1 mW to 300 mW.

In another exemplary embodiment, the invention produces specific wavelengths in the form of linear waves, including, but not limited to, sine, square, triangular, and saw tooth waves. Additional wave types can be produced, including, but not limited to, solution waves, a self-reinforcing solitary wave (a wave packet or pulse) that maintains its shape while it travels at constant speed, and longitudinal waves capable of passing through tissue from one side to another with no loss of strength. The utilization of a single wave type or combination of wave types produces a wavelength with no degradation to wave shape allowing the energy produced from the wave to penetrate any desired depth of biological tissue.

The cover lens made out of various type of materials but not limited to plastic, Quartz crystal, glass, and prisms may be used, but limited to shapes, size, or refractive abilities. This invention produces a scalar wave, as well as any other waves known via refractive lenses and various configurations of lenses.

Using the applicable control mechanism, such as by wireless or wired connection with a computing device operating a control program, a touchpad monitor, a cellphone app, or the like on or connected to the device, the operator or user can control the frequency, amplitude, and phase of the wavelengths through a digital interface. The operator can select the frequency (pulse), wavelength, amplitude, and wave type associated with each light-emitting source. This phase relationship allows for each channel to be specifically programmed with frequency and peak-to-peak amplitude allowing multiple channels to operate at a different frequency (pulse) and amplitude. Thus, the phototherapy device can produce multiple wavelengths, multiple wave types, multiple frequencies (pulses), and multiple amplitudes.

In one embodiment, the control box comprises a front and back, which may be glued, affixed or screwed together. The interior comprises the control electronics and light power supply, a wireless chip, a "handshake" chip, a MP3 player, and a RF or Bluetooth smart chip, Li-Fi for identification of the unit. The control box may comprise a power indicator, a power switch, an USB port (for updating software) and other controls, switches and ports as necessary. The control box may be made in a variety of colors, sizes, and configurations.

In a further embodiment, the present invention incorporates the geometric configuration of single light technology or multiple light technologies, wavelength, amplitude and power output, referred to as the array. The geometric configuration is not limited to any single configuration and can include any geometric configuration of wavelengths, power output, amplitude, and wave types. The array is engineered to produce multiple wavelengths, power outputs, amplitudes and wave types producing therapeutic benefits to human brain and eye. This is accomplished by utilizing expandable software, smart chips, adaptive lenses, and light producing technology that is completely scalable and configurable to operator needs. The geometric arrangement of the light technology is not limited to any single geometric configuration, wavelength, power output, amplitude, or wave type. The array can be configured to support any geometric configuration of multiple wavelengths, multiple power outputs, multiple amplitudes, or multiple wave types.

In one particular embodiment, the present invention will only work with specific control boxes, accessories, or computing devices, which can be self-identifying through "handshake" communications technology. Utilizing handshake technology will only pair specific units to specific accessories. A specific circuit board chip may be utilized in each and every piece of equipment. These chips include a one-of-a-kind code that forms a unique link to each other. The circuit board may be a variable frequency circuit board. Specific RF chips may be installed in each and every unit so that identifications can be placed into each piece of equipment to identify purchase dates and other necessary information.

In yet a further embodiment, the invention is equipped with an USB or mini-USB port and wireless circuit board that will operate and control peripheral devices by the digital interface of the phototherapy device. Peripheral devices are not limited to and include light technology devices and any device that generates frequency or electrical pulse. The peripheral devices will be activated upon a passcode entered into the digital interface of the phototherapy device. In addition, an internal solid-state hard drive may be included in each unit to provide storage for music and other audio files.

In one exemplary embodiment, the device works in conjunction with a software application operating on a smart phone, tablet, a fitness band (e.g., "Fit Bit"), or other mobile computing device. The combination allows the user to determine the quality of their sleep for the night (or a series of nights), including motions, temperature, REM sleep patterns, and the like. The combination would allow the user to control the device and send specific frequencies to the microcontroller on the middle layer circuit board through the application. The application would give the microcontroller the ability to move through a library of frequencies to deliver an assort of programs or data, including specific programming to address time zone acclimatization, fatigue, seasonal disorders, weight loss, deep sleep, and relaxation responses.

In order to provide a context for the various aspects of the invention, the following discussion provides a brief, general description of a suitable computing environment in which the various aspects of the present invention may be implemented. A computing system environment is one example of a suitable computing environment, but is not intended to suggest any limitation as to the scope of use or functionality of the invention. A computing environment may contain any one or combination of components discussed below, and may contain additional components, or some of the illustrated components may be absent. Various embodiments of the invention are operational with numerous general purpose or special purpose computing systems, environments or configurations. Examples of computing systems, environments, or configurations that may be suitable for use with various embodiments of the invention include, but are not limited to, personal computers, laptop computers, computer servers, computer notebooks, hand-held devices, microprocessor-based systems, multiprocessor systems, TV set-top boxes and devices, programmable consumer electronics, cell phones, personal digital assistants (PDAs), tablets, smart phones, touch screen devices, smart TV, internet enabled appliances, internet enabled security systems, internet enabled gaming systems, internet enabled watches; internet enabled cars (or transportation), network PCs, minicomputers, mainframe computers, embedded systems, virtual systems, distributed computing environments, streaming environments, volatile environments, and the like.

Embodiments of the invention may be implemented in the form of computer-executable instructions, such as program code or program modules, being executed by a computer, virtual computer, or computing device. Program code or modules may include programs, objects, components, data elements and structures, routines, subroutines, functions and the like. These are used to perform or implement particular tasks or functions. Embodiments of the invention also may be implemented in distributed computing environments. In such environments, tasks are performed by remote processing devices linked via a communications network or other data transmission medium, and data and program code or modules may be located in both local and remote computer storage media including memory storage devices such as, but not limited to, hard drives, solid state drives (SSD), flash drives, USB drives, optical drives, and internet-based storage (e.g., "cloud" storage).

In one embodiment, a computer system comprises multiple client devices in communication with one or more server devices through or over a network, although in some cases no server device is used. In various embodiments, the network may comprise the Internet, an intranet, Wide Area Network (WAN), or Local Area Network (LAN). It should be noted that many of the methods of the present invention are operable within a single computing device.

A client device may be any type of processor-based platform that is connected to a network and that interacts with one or more application programs. The client devices each comprise a computer-readable medium in the form of volatile and/or nonvolatile memory such as read only memory (ROM) and random access memory (RAM) in communication with a processor. The processor executes computer-executable program instructions stored in memory. Examples of such processors include, but are not limited to, microprocessors, ASICs, and the like.

Client devices may further comprise computer-readable media in communication with the processor, said media storing program code, modules and instructions that, when executed by the processor, cause the processor to execute the program and perform the steps described herein. Computer readable media can be any available media that can be accessed by computer or computing device and includes both volatile and nonvolatile media, and removable and non-removable media. Computer-readable media may further comprise computer storage media and communication media. Computer storage media comprises media for storage of information, such as computer readable instructions, data, data structures, or program code or modules. Examples of computer-readable media include, but are not limited to, any electronic, optical, magnetic, or other storage or transmission device, a floppy disk, hard disk drive, CD-ROM, DVD, magnetic disk, memory chip, ROM, RAM, EEPROM, flash memory or other memory technology, an ASIC, a configured processor, CDROM, DVD or other optical disk storage, magnetic cassettes, magnetic tape, magnetic disk storage or other magnetic storage devices, or any other medium from which a computer processor can read instructions or that can store desired information. Communication media comprises media that may transmit or carry instructions to a computer, including, but not limited to, a router, private or public network, wired network, direct wired connection, wireless network, other wireless media (such as acoustic, RF, infrared, or the like) or other transmission device or channel. This may include computer readable instructions, data structures, program modules or other data in a modulated data signal such as a carrier wave or other transport mechanism. Said transmission may be wired, wireless, or both. Combinations of any of the above should also be included within the scope of computer readable media. The instructions may comprise code from any computer-programming language, including, for example, C, C++, C #, Visual Basic, Java, and the like.

Components of a general purpose client or computing device may further include a system bus that connects various system components, including the memory and processor. A system bus may be any of several types of bus structures, including, but not limited to, a memory bus or memory controller, a peripheral bus, and a local bus using any of a variety of bus architectures. Such architectures include, but are not limited to, Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computing and client devices also may include a basic input/output system (BIOS), which contains the basic routines that help to transfer information between elements within a computer, such as during start-up. BIOS typically is stored in ROM. In contrast, RAM typically contains data or program code or modules that are accessible to or presently being operated on by processor, such as, but not limited to, the operating system, application program, and data.

Client devices also may comprise a variety of other internal or external components, such as a monitor or display, a keyboard, a mouse, a trackball, a pointing device, touch pad, microphone, joystick, satellite dish, scanner, a disk drive, a CD-ROM or DVD drive, or other input or output devices. These and other devices are typically connected to the processor through a user input interface coupled to the system bus, but may be connected by other interface and bus structures, such as a parallel port, serial port, game port or a universal serial bus (USB). A monitor or other type of display device is typically connected to the system bus via a video interface. In addition to the monitor, client devices may also include other peripheral output devices such as speakers and printer, which may be connected through an output peripheral interface.

Client devices may operate on any operating system capable of supporting an application of the type disclosed herein. Client devices also may support a browser or browser-enabled application. Examples of client devices include, but are not limited to, personal computers, laptop computers, personal digital assistants, computer notebooks, hand-held devices, cellular phones, mobile phones, smart phones, pagers, digital tablets, Internet appliances, and other processor-based devices. Users may communicate with each other, and with other systems, networks, and devices, over the network through the respective client devices.

Thus, it should be understood that the embodiments and examples described herein have been chosen and described in order to best illustrate the principles of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art.

What is claimed is:

1. A mask, comprising:
an opaque outer layer, wherein said outer layer is made of foam or memory foam;
an inner layer comprising a top, a bottom, and two eyeholes, wherein said inner layer is made of memory foam;
a plurality of interchangeable light source boards, each of said plurality of light source boards comprising a plurality of light sources on one side, and configured to be positioned between the outer layer and the inner layer such that light from said plurality of light sources is directed through said eyeholes and focuses onto a respective eye area,
wherein said plurality of light sources on respective light source boards comprises a different configuration or pattern of light sources;
an aroma-carrying strip attached to the bottom of the inner layer;
a scan disk drive; and
one or two earbuds or earphones with a plurality of light sources on said earbuds or said earphones;
wherein the light sources are programmed to display different colors and intensities for different treatments; and
wherein the configuration or pattern of light sources includes a variety of angled positions, each angled position being defined with respect to the respective light source board, in a manner allowing bi-directional crisscrossing of emitted light.

2. The mask of claim 1, further comprising a middle layer positioned between said outer layer and said inner layer, wherein each of said plurality of interchangeable light source boards is removably attached to said middle layer when positioned between the outer layer and the inner layer.

3. The mask of claim 1, wherein said light sources comprise at least one of light-emitting diodes (LEDs) or laser diodes.

4. The mask of claim 1, further comprising a circuit control board with a rechargeable energy source and a communications port.

5. The mask of claim 1, wherein the light sources are controlled by the respective circuit control board.

6. The mask of claim 1, further comprising a strap attached to a sleeve or a bag, said sleeve or bag totally enclosing said mask.

7. The mask of claim 6, wherein said sleeve or said bag comprises two eyeholes.

8. The mask of claim 1, further comprising an eyeglass clip.

9. The mask of claim 1, wherein the mask further receives information through wireless communication technology.

10. The mask of claim 1, wherein the wireless communication technology comprises Bluetooth.

* * * * *